United States Patent [19]

Suh et al.

[11] Patent Number: 5,200,416

[45] Date of Patent: Apr. 6, 1993

[54] CYCLIC AMIDES

[75] Inventors: John T. Suh, Greenwich, Conn.;
Jerry W. Skiles, Tuckahoe, N.Y.;
Bruce E. Williams, Cottage Grove,
Minn.

[73] Assignee: USV Pharmaceutical Corporation,
Tuckahoe, N.Y.

[21] Appl. No.: 148,083

[22] Filed: May 12, 1980

[51] Int. Cl.$^5$ .................. A61K 31/47; C07D 217/16
[52] U.S. Cl. .................................. 514/307; 546/146; 546/147
[58] Field of Search ................ 546/146, 147; 424/258; 514/307

[56] References Cited

U.S. PATENT DOCUMENTS 4,251,444  2/1981  Freed et al. .......................... 546/141
4,256,751  3/1981  Hayashi et al. ..................... 546/147

Primary Examiner—C. Warren Ivy
Assistant Examiner—James H. Turnipseed
Attorney, Agent, or Firm—Scully, Scott, Murphy & Presser

[57] ABSTRACT

Compounds of the formula

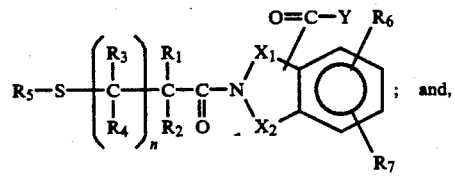

; and, wherein:
$R_1$, $R_2$, $R_3$, $R_4$, $R_6$, and $R_7$ are independently hydrogen or lower alkyl.
$R_5$ is hydrogen, lower alkyl, rad alkanoyl having 1 to 6 carbon atoms.
Y is OH or OM wherein M is a pharmaceutically acceptable cation, and
n is an integer from 0 to 1, and
$X_1$ and $X_2$ are independently $(CR_8R_9)_m$
wherein $R_8$ and $R_9$ are independently hydrogen or lower alkyl and m is an integer from 1 to 5 are potent angiotensin converting enzyme inhibitors and possess antihypertensive activity.

42 Claims, No Drawings

CYCLIC AMIDES

This invention relates to new chemical compounds having valuable pharmaceutical activity. It particularly relates to amides having antihypertensive and angiotensin converting enzyme inhibitory activity, having the structure:

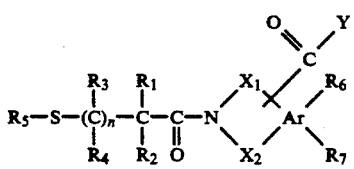

wherein:

$R_1$, $R_2$, $R_3$ and $R_4$ are independently hydrogen, alkyl, alkenyl, alkynyl, aryl, heteroaryl, aralkyl, heteroaralkyl, cycloalkyl, polycycloalkyl, and heterocycloalkyl;

n is an integer from 0 to 4 inclusive;

$R_5$ is hydrogen, alkyl, aralkyl, aryl, hydroxyalkyl, aminoalkyl, alkanoyl, aryloyl, arylalkanoyl, hydroxyalkanoyl carboxyalkanoyl, aminoalkanoyl, cyano, amino, alkylamino, aryl-amino, amidino, alkylamidino, arylamidino, and ZS-, $ZS(CR_1R_2)_n$-or or ZSCO- wherein Z is alkyl, aryl, aralkyl or a radical of the formula

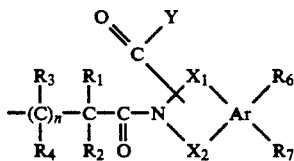

wherein $R_1$, $R_2$, $R_3$, $R_4$, $R_6$, $R_7$, n, $X_1$, $X_2$ and Y are as herein defined:

Y is OH, OM, OR, $NR_1R_2$, $-NR_1-(CR_1R-)_n-CO-Y^1$ wherein M is a pharmaceutically acceptable cation, $R_1$, $R_2$ and n are as herein defined, and $Y_1$ is OH, OM, $OR_1$ or $NR_1R_2$;

$X_1$ and $X_2$ are independently S, SO, $-SO_2$, $NR_1$, chemical bond, O, $(CR_8R_9)_m$, $-CR_8=CR_9-$, and CHOH, with the proviso that at least one of $X_1$ and $X_2$ be $(CR_8R_9)_m$, wherein $R_8$ and $R_9$ are independently hydrogen or lower alkyl, and m is an integer from 0 to 5.

Ar is a divalent arylene or heteroarylene; and $R_6$ and $R_7$ are independently hydrogen, alkyl, halo, cyano, hydroxy, alkoxy, amino, alkylamino, dialkylamino, mercapto, alkylmercapto, nitro, trifluoromethyl, carboxy, carbalkoxy, COY, and $NHCONHR_1$, wherein $R_1$ and Y are as herein defined.

The alkyl groups per se and in the alkyl moiety in aralkyl, cycloalkyl-alkyl, polycycloalkyl-alkyl, heteroaryl-alkyl and the like, and, in alkoxy, alkylmercapto, alkanoyl, carbalkoxy, alkylamino and dialkylamino, may be straight chained or branched and are preferably alkyl groups containing from 1 to 20 carbons. Such groups include methyl, ethyl, propyl, isopropyl, butyl, isobutyl, amyl, iso-amyl, hexyl, octyl, dodecyl, and the like. Preferably the alkyl groups are lower alkyl containing from 1 to 6 carbon atoms.

The alkenyl and alkynyl groups may also be branched or straight-chained and contain from 2 to 6 carbon atoms. Such groups include vinyl, ethynyl, propenyl, allyl, isopropenyl, and the like.

These alkyl, alkenyl, and alkynyl groups may carry substituents such as hydroxy, alkoxy, amino, alkylamino, dialkylamino, mercapto, alkylmercapto, halo, and the like.

The cycloalkyl, polycycloalkyl, aryl, heteroaryl, aryalkyl, fused aryl-cycloalkyl, groups and the like contain from 3 to 16 carbon atoms and may carry substituents such as lower alkyl, alkenyl, alkynyl, hydroxy, mercapto, amino, alkoxy, alkylmercapto, alkylamino, dialkylamino, halo, trifluoromethyl and the like. The groups include such radicals as cyclopropyl, cyclobutyl, cyclopentyl, cyclohexyl, cycloheptyl, adamantyl, norbornyl, phenyl, tolyl, benzyl, penethyl, dimethoxyphenyl, hydroxybenzyl, indanyl, naphthyl, tetrahydronaphthyl, decahydronaphthyl, pyridyl, quinolyl, pyrrolidyl, pyrrolyl, morpholinyl, furyl, furfuryl, tetrahydrofurfuryl, benzimidazolyl, thienyl, imidazolyl, and the like.

The halo groups include fluoro, chloro, bromo and iodo.

The pharmaceutically acceptable cations include both monovalent and polyvalent metals such as, for example, sodium, potassium, calcium, magnesium, iron and the like, and anmonium cations derived from ammonia, primary, secondary and tertiary amines.

The preferred compounds of the invention are those wherein one of $X_1$ and $X_2$ is $CH_2$, and the other is $-CH_2-CHR_8-$. Ar is o-phenylene, n is 0 or 1, $R_1$, $R_3$, $R_4$, $R_6$ and $R_7$ are hydrogen, Y is hydroxy, $R_2$ is methyl, $R_5$ is hydrogen or acetyl, and $R_8$ is hydrogen or lower alkyl.

It is known to those skilled in the art that those amides of the present invention having ar: asymmetric carbon atom may exist in racemic or optically active levo or dextro forms. All of these forms are contemplated within the scope of this invention.

The compounds of the present invention may be obtained by the reaction of a compound of the structure:

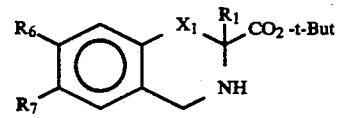

with a carboxylic acid or carboxylic acid halide of the structure;

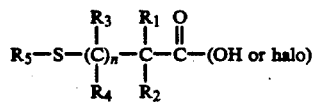

to give the compound:

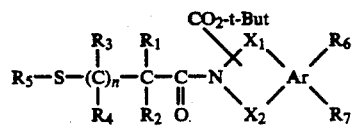

followed by the hydrolysis of the t-butyl ester to yield a free carboxylic acid, one of the compounds of the present invention.

By appropriate reactions various compounds can be made using the above scheme. For example, when $R_5$ is acetyl the compound may be hydrolyzed to give a compound where $R_5$ is hydrogen and this compound may in turn be converted by the reaction with appropriate acyl halides to give other desired $R_5$ substituents.

The free carboxylic acid (Y is OH) may be converted to salts, esters and amides. The disulfides are prepared by mild oxidation of the corresponding mercapto acid with iodine or oxygen.

Other useful synthetic procedures for preparation of compounds of the present invention are outlined in Methods A, B, C and D.

In Method A the compounds are obtained by direct acylation of an appropriate amino acid or an ester of an amino acid.

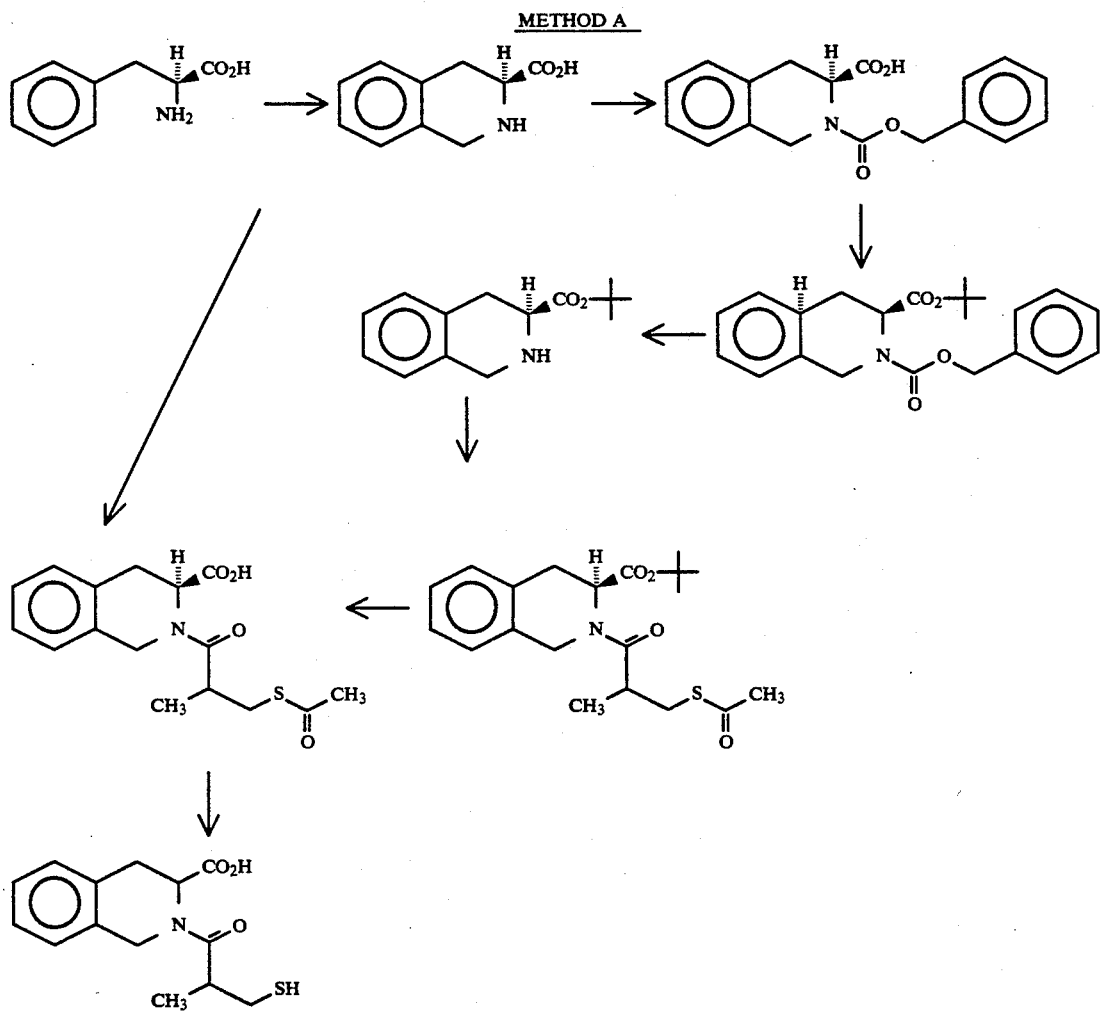

METHOD A

Method B illustrates the preparation of $\beta$-carboline analogs.

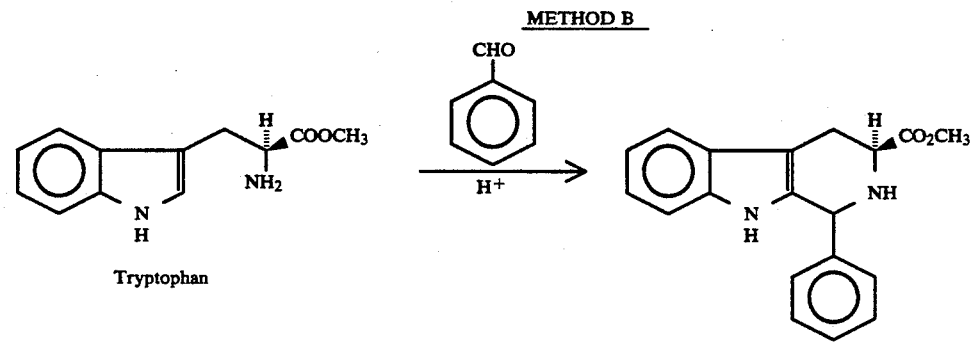

METHOD B

-continued
METHOD B
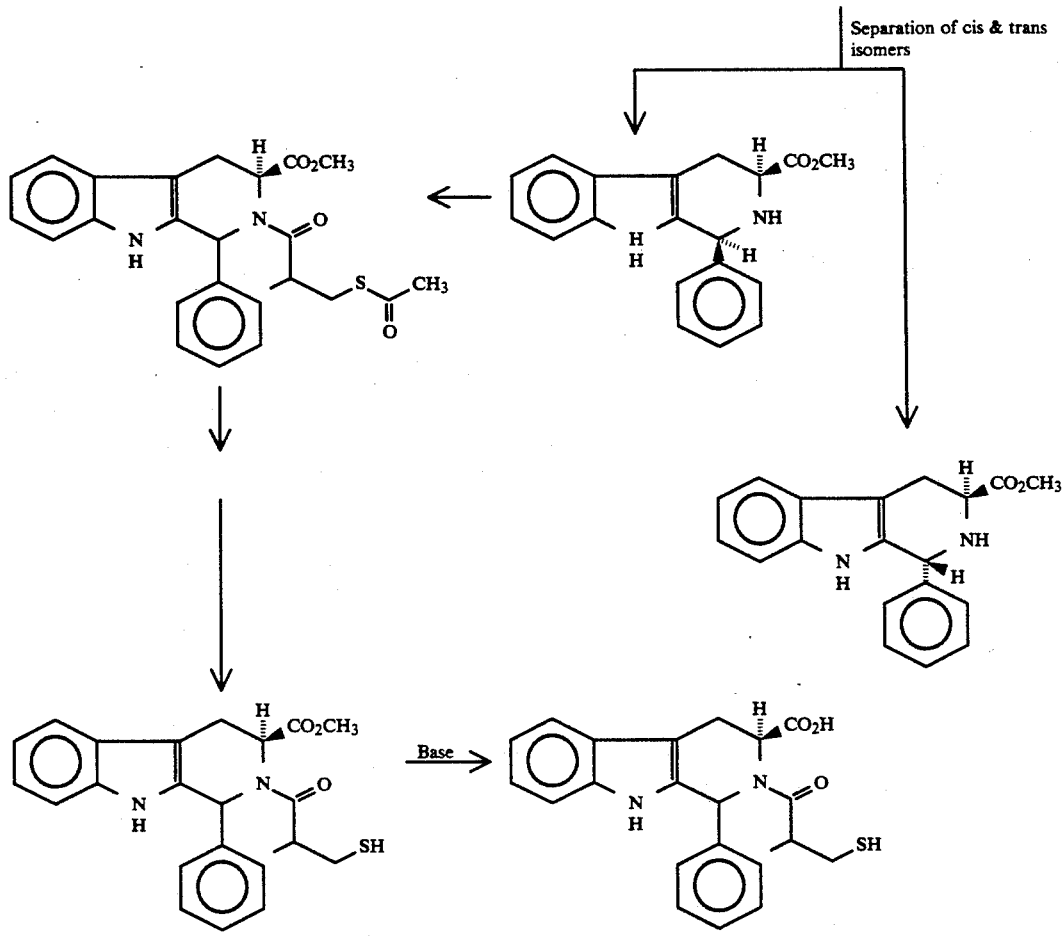
Methods C and D illustrate the preparation of certain heterocyclic analogs.
METHOD C
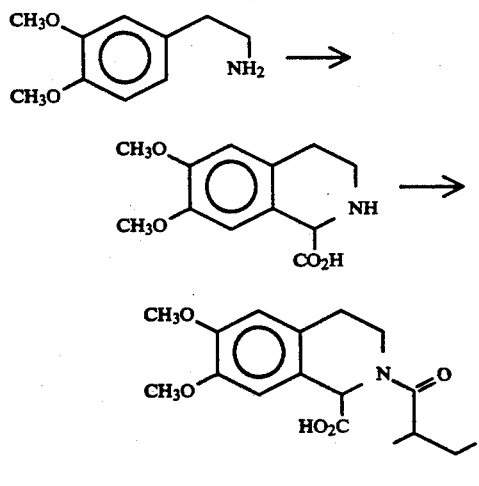
METHOD D
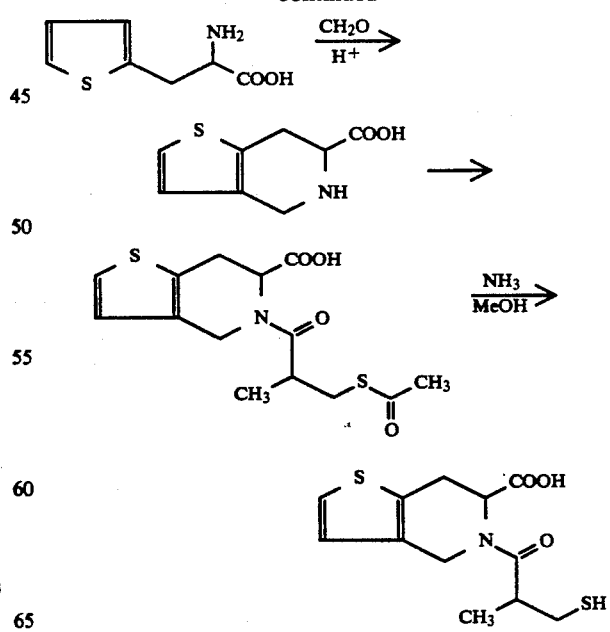
The desired intermediates may be prepared by well-known reactions.

The invention will be more fully illustrated in the examples which follow. These examples are given by way of illustration and are not to be considered as limiting.

EXAMPLE I

L-1,2,3,4-Tetrahydroisoquinoline-3-carboxylic Acid

A suspension of L-phenylalanine (75 g, 0.455 mole) in concentrated hydrochloric acid (488 ml) and 37% formalin (165 ml) was heated to a gentle reflux with vigorous stirring for thirty minutes. After this time, another portion of 37% formalin (75 ml) and concentrated hydrochloric acid (165 ml) was added. Stirring and heating were continued for four hours. The reaction mixture was cooled to room temperature and the solid which formed was filtered and washed with a small amount of methanol to afford the hydrochloride as a colorless solid (68.9 g, 71%), m.p. 291°–294°.

EXAMPLE II

N-Benzylcarbethoxy-L-1,2,3,4-tetrahydroisoquinoline-3-carboxylic acid

L-1,2,3,4-Tetrahydroisoquinoline-3-carboxylic acid hydrochloride (58.8 g, 0.275 mole) was dissolved in 1N sodium hydroxide (600 ml) and the resulting solution was cooled in an ice bath. Benzyl chloroformate (39.0 ml, 0.263 mole) was added dropwise. After all the benzyl chloroformate was added (30 min.) stirring was continued for an hour at room temperature and then another portion of 1N sodium hydroxide (100 ml) was added. Stirring was continued for another 2½ hours. The reaction mixture was acidified to pH 4 with concentrated hydrochloric acid and the product was extracted into chloroform. The organic phase was washed twice with water and dried over magnesium sulfate. Filtration and evaporation of the solvent afforded a colorless oil (86.3 g, 91.5%) which was used without further purification.

EXAMPLE III tert-Butyl N-benzylcarbethoxy-L-(1,2,3,4-tetrahydroisoquinoline)-3-carboxylate N-Benzylcarbethoxy-L-1,2,3,4-tetrahydroisoquinoline-3-carboxylic acid (46.5 g, 0.150 mole) was dissolved in methylene chloride (1000 ml) and concentrated sulfuric acid (7 ml) was added. The resulting mixture was cooled in a dry-ice acetone bath to $-30°$ and then isobutylene was bubbled through the solution for three hours. The reaction vessel was lightly stoppered with a pressure releasing valve and stored overnight at room temperature. The reaction mixture was basified cautiously by the dropwise addition of 10% aqueous potassium carbonate. The organic phase was separated and washed once more with 10% $K_2CO_3$ and then twice with water. The organic extract was dried over magnesium sulfate. Filtration and evaporation of the solvent afforded a pale yellow oil (45.3 g, 82.4%) which was used without further purification.

EXAMPLE IV tert-Butyl L-(1,2,3,4-tetrahydroisoquinoline)-3-carboxylate tert

Butyl N-benzylcarbethoxy-L-(1,2,3,4-tetrahydroisoquinoline)-3-carboxylate (45 g, 0.123 mole) was dissolved in absolute ethanol (600 ml) and 10% Pd/C (4 grams) was added. The resulting mixture was hydrogenated in a low pressure Parr shaker at a pressure of 50 psi for sixteen hours. The catalyst was filtered off and the solvent was evaporated to afford crude product as a pale yellow oil (24.8 g, 86.4%) which was used without further purification.

EXAMPLE V tert-Butyl N-(3'-acetylthio-2'-methylpropanoyl)-L-(1,2,3,4-tetrahydroisoquinoline)-3-carboxylate To a solution of tert-butyl L-(1,2,3,4-tetrahydroisoquinoline)-3-carboxylate (8.1 g, 0.0349 mole) and 3-acetylthio-2-methylpropionic acid (5.6 g, 0.0346 mole) in methylene chloride (250 ml) chilled in an ice bath was added dicyclohexylcarbodiimide (7.2 g, 0.0350 mole). The resulting mixture was stirred with external cooling for 30 minutes and then for approximately three hours at room temperature. Precipitated dicyclohexylurea was filtered and washed with a small amount of methylene chloride. Concentration of the filtrate afforded crude product as a pale yellow oil which was used without further purification.

EXAMPLE VI

N-(3'-Acetylthio-2'-methylpropanoyl)-L-(1,2,3,4-tetrahydroisoquinoline)-3-carboxylic acid Crude tert-butyl N-(3'-acetylthio-2'-methylpropanoyl)-L-(1,2,3,4-tetrahydroisoquinoline)-3-carboxylate (14 g, 0.0371 mole) was dissolved in a mixture of anisole (25 ml) and trifluoroacetic acid (75 ml). The resulting solution was stirred at room temperature for approximately one hour. Trifluoroacetic acid was removed in vacuo and the residue was distributed between ethyl acetate and saturated sodium bicarbonate. The aqueous bicarbonate phase was separated and washed twice with ethyl acetate and then acidified cautiously to pH 2 to 4 with concentrated hydrochloric acid. The precipitated product was extracted several times into chloroform and the combined organic extract was washed twice with water, dried over magnesium sulfate, filtered and evaporated to give a pale yellow oil (7.3 g). This crude product was purified by high pressure liquid chromatography using the mixture of n-hexane/ethyl acetate/acetic acid (30:60:1) as eluant to give pure product as a colorless oil (5.9 g). The product was characterized as its dicyclohexylamine (DCHA) salt, which was prepared in ether, to give colorless crystals, m.p. 161°–163°.

EXAMPLE VII

N-(3'-Mercapto-2'-methylpropanoyl)-L-(1,2,3,4-tetrahydroisoquinoline)-3-carboxylic acid Anhydrous ammonia was bubbled for fifteen minutes through methanol (100 ml) and the resulting saturated solution was added to N-(3'-acetylthio-2'-methylpropanoyl)-L-(1,2,3,4-tetrahydroisoquinoline-3-carboxylic acid (2.0 g, 0.00623 mole) and placed under nitrogen. The reaction was stirred at room temperature for one hour. The solvent was removed in vacuo and the residue was applied to a column of AG-50W-X2 cation exchange resin and eluted with methanol. Methanol was evaporated and the residue was dissolved in chloroform. The chloroform was washed once with water and dried over magnesium sulfate. Filtration and evaporation of the solvent afforded a colorless oil (1.7 g, 98%). The free acid was converted to its DCHA salt in ether to afford colorless crystals, m.p. 146°-147°. The product was characterized as its DCHA salt.

EXAMPLE VIII 2-(3'-Acetylthio-2'-methylpropanoyl)-1-phenyl-3-carbomethoxy-1,2,3,4-tetrahydro-8-carboline 1-Phenyl-3-carbomethoxy-1,2,3,4-tetrahydro-β-carboline (10 g, 0.0327 mole) and triethylamine (4.1 g, 0.04 mole) were dissolved in acetonitrile (250 ml) and the resulting mixture was chilled in an ice bath. 3-Acetylthio-2-methylpropionyl chloride (6.5 g, 0.036 mole) was added portionwise. After all the acid chloride was added the ice bath was removed and the mixture was stirred at room temperature under nitrogen for two and a half hours. The solvent was evaporated and the residue was dissolved in chloroform. The chloroform was washed with water, 5% aqueous NaOH, 5% aqueous HCl, and water. The chloroform was dried over magnesium sulfate, filtered and evaporated to give the crude product as a lightly colored oil. The product was further purified by chromatography on silica-gel ($CH_2Cl_2$) to give the pure product as a colorless oil (9.6 g, 65%).

EXAMPLE IX 2-(3'-Mercapto-2'-methylpropanoyl)-1-phenyl-3-carbomethoxy-1,2,3,4-tetrahydro-β-carboline 2-(3'Acetylthio-2'-methylpropanoyl)-1-phenyl-3-carbomethoxy-1,2,3,4-tetrahydro-β-carboline (2 g, 0.045 mole) was dissolved in methanol (75 ml) and anhydrous ammonia was bubbled through the solution for 15 minutes. The reaction was placed under nitrogen and stirring was continued at room temperature for one hour. The methanol was evaporated and the residue was applied to a cation exchange column (methanol). The methanol was evaporated and the residue was dissolved in chloroform, washed with water, dried over magnesium sulfate, filtered and evaporated to give the product as a colorless oil (1.6 g, 88%).

EXAMPLE X

N-(3'-Acetylthio-2'-methylpropanoyl)-L-(1,2,3,4-tetrahydroiso-quinoline)-3-carboxylic acid To a stirred suspension of L-1,2,3,4-tetrahydroisoquinoline-3-carboxylic acid (40.0 g, 187.2 mmoles) in approximately 1 liter of p-dioxane and water (200 ml) was added triethylamine (78 ml, 560.8 mmoles) followed by dropwise addition of 3-acetylthio-2-methylpropionoyl chloride (33.8 g, 187.2 mmoles). The mixture became mostly homogeneous as the reaction proceeded. After approximately three hours a small amount of insoluble material was filtered off and the filtrate was concentrated on a rotary evaporator. The resulting solution was diluted with water and acidified to pH 2 with concentrated HCl and extracted into ethyl acetate. The ethyl acetate solution was washed twice with water, once with brine, dried over magnesium sulfate, filtered and evaporated to yield approximately 55 g of oil. The crude material was separated by preparative chromatography eluting with 2% acetic acid, 40% ethyl acetate, and 60% hexane to yield 30.2 g (50.2%) of pure material.

Following the procedure described in the above examples, the following additional compounds were prepared:

N-(3'-Acetylthio-2'-methylpropanoyl)-L-6,7-dihydroxy-1,2,3,4-tetrahydroisoquinoline-3-carboxylic acid N-(3'-Acetylthio-2'-methylpropanoyl)-L-6,7-dimethoxy-1,2,3,4-tetrahydroisoquinoline-3-carboxylic acid N-(3'-Acetylthio-2'-methylpropanoyl)-L-7-chloro-1,2,3,4-tetrahydroisoquinoline-3-carboxylic acid N-(3'-Mercapto-2'-methylpropanoyl)-L-6,7-dimethoxy-1,2,3,4-tetrahydroisoquinoline-3-carboxylic acid N-(3'-Mercapto-2'methylpropanoyl)-L-7-hydroxy-6-methoxy-1,2,3,4-tetrahydroisoquinoline-3-carboxylic acid N-(3'-Acetylthio-2'-methylpropanoyl)-6,7-dimethoxy-1,2,3,4-tetrahydroisoquinoline-1-carboxylic acid N-(3'Mercapto-2'-methylpropanoyl)-L-3-methyl-1,2,3,4-tetrahydroisoquinoline-3-carboxylic acid 2-(3'-Acetylthio-2'-methylpropanoyl)-6-fluoro-1,2,3,4-tetrahydro-8-carboline-3-carboxylic acid 2-(3'-mercapto-2'-methylpropanoyl)-1-methyl-3-1,2,3,4-tetrahydro-8-carboline-3-carboxylic acid N-(3'-Acetylthio-2'-methylpropanoyl)-L-1-methyl-1,2,3,4-tetrahydroisoquinoline-3-carboxylic acid N-(2'-Mercapto-2'-methylpropanoyl)-L-L-methyl-3,4-terranydroisoquinoline-3-carboxylic acid N-(3'-Acetylthio-2'-methylpropanoyl)-1-(3'4'-dimethoxy-phenyl)-1,2,3,4-tetrahydroisoquinoline-3-carboxylic acid N-(3'-Trimethylacetylthio-2'-methylpropanoyl)-1,2,3,4-tetrahydrothieno[3,2-C]-pyridine-3-carboxylic acid 2'6; -Dichlorobenzoylthio-2'-methylpropanoyl-1,3-benzothiazine-2-carboxylic acid N-(2'-Acetylthiopropanoyl)-benzo-2-azacycloheptane-3-carboxylic acid N-(3'-Acetylthio-2'-methylpropanoyl)-1,2-dihydroisoquinoline-1-carboxylic acid The compounds of the present invention exhibit potent angiotensin enzyme inhibitory activity. Such activity indicates that the compounds of the present invention are useful in the treatment of hypertension. When administered intraperitoneally to spontaneously hypertensive rats the compounds of the present invention effected a reduction in the blood pressure of about 20 to 30% at a range of about 100 mg /kg.

The compounds of the present invention may be administered orally or parenterally in the treatment of hypertension, and it will be within the professional judgement and skill of the practitioner to determine the exact amount to be administered.

We claim:

1. A compound of the formula

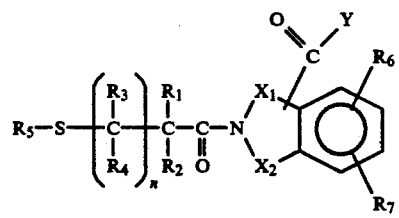

wherein
$R_1$, $R_2$, $R_3$, $R_4$, $R_6$ and $R_7$ are independently hydrogen or lower alkyl having 1–6 carbon atoms;
$R_5$ is hydrogen, lower alkyl having 1 to 6 carbon atoms, or alkanoyl having 1 to 6 carbon atoms;

Y is OH or OM wherein M is a pharmaceutically acceptable cation;

n is an integer from 0 to 1, and one of $X_1$ and $X_2$ is $(CR_8R_9)$ and the other is $(CR_8R_9)_2$ wherein $R_8$ and $R_9$ are independently hydrogen or lower alkyl having 1 to 6 carbon atoms.

2. A compound according to claim 1 wherein Y is OH.

3. A compound according to claim 2 wherein $R_1$, $R_6$ and $R_7$ are hydrogen, $R_2$ is methyl and $R_5$ is hydrogen or alkanoyl having from 1 to 6 carbon atoms.

4. A compound according to claim 1 wherein $x_1$ in —$CHR_8$—$CH_2$—wherein $R_8$ is hydrogen or methyl.

5. A compound according to claim 4 wherein $X_2$ is —$CH_2$—.

6. A compound according to claim 5 wherein the integer n is 0.

7. A compound according to claim 6 having the structure

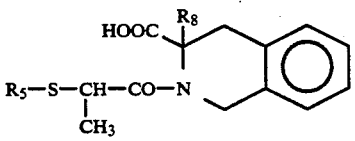

8. A compound according to claim 7 wherein $R_8$ is hydrogen and $R_5$ is hydrogen, pivaloyl, or t-butyl-acetyl.

9. A compound according to claim 7 wherein $R_8$ is methyl.

10. A compound according to claim 5 wherein the integer n is 1.

11. A compound according to claim 10 wherein $R_3$ and $R_4$ are hydrogen.

12. A compound according to claim 11, having the structure

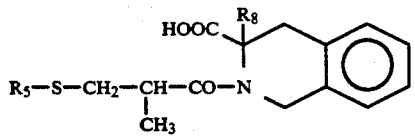

13. A compound according to claim 12 wherein $R_5$ is hydrogen, pivaloyl or t-butyl-acetyl and $R_8$ is hydrogen.

14. A compound according to claim 12 wherein $R_8$ is methyl.

15. A compound according to claim 9 wherein $R_5$ is hydrogen.

16. A compound according to claim 14 wherein $R_5$ is hydrogen.

17. A compound according to claim 12 wherein
$R_5$ is acetyl and
$R_8$ is hydrogen.

18. The compound according to claim 1 having the formula

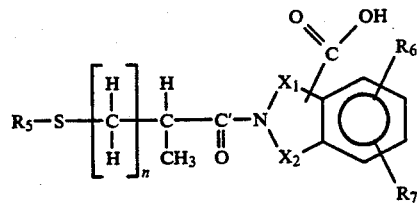

wherein
one of $X_3$ and $X_2$ is $CH_2$, and the other is $CH_2CHR_8$,
n is 0 or 1,
$R_5$ is hydrogen or acetyl and
$R_8$ is hydrogen or lower alkyl, or a pharmaceutically acceptable salt thereof.

19. The compound according to claim 18 in which $R_5$ is hydrogen.

20. The compound according to claim 18 in which $R_8$ is hydrogen.

21. The racemic or optically active compound of claim 1.

22. A method of reducing the blood pressure in mammals having hypertension which comprises administering an effective amount of a compound according to claim 1.

23. A hypotensive composition which comprises an amount of a compound according to claim 18, or a pharmaceutically acceptable salt thereof and which amount is sufficient when administered to a warm blooded animal, to provide an effective amount thereof in said animal, and a pharmaceutically acceptable carrier therefor.

24. A compound of the formula:

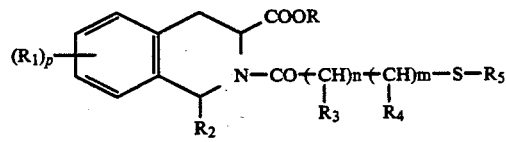

wherein:
R=H, alkyl or alkali metal selected from the group consisting of sodium and potassium;
$R_1$=H;
$R_2$=H, alkyl;
$R_3$=H, alkyl, benzyl;
$R_4$=H, alkyl;
$R_5$=H, alkanoyl, aroyl;
n=0, 1, 2;
m=0, 1, 2;
p=1, 2, 3;
or a pharmaceutically acceptable salt thereof.

25. A compound of the formula:

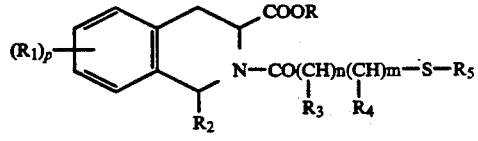

wherein:
R=H, alkyl or alkali metal selected from the group consisting of sodium and potassium;
$R_1$=H;
$R_2$=H, alkyl;

R₃=alkyl;
R₄=H;
R₅=H, alkanoyl, aroyl;
n=1;
m=1;
p=1, 2, 3;
or a pharmaceutically acceptable salt thereof.

26. A compound of the formula:

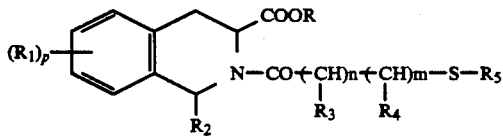

wherein
R=H, alkyl or alkali metal selected from the group consisting of sodium and potassium;
R₁=alkyl, halo, cyano, hydroxy, alkoxy, amino, alkylamino, alkylamino, mercapto, alkylmercapto, nitro, trifluoromethyl, carboxy, carbalkoxy;
R₂=H, alkyl;
R₃=H, alkyl, benzyl;
R₄=H, alkyl;
R₅=H, alkanoyl, aroyl;
n=0, 1, 2;
m=0, 1, 3;
p=1, 2, 3;
or a pharmaceutically acceptable salt thereof.

27. A compound of the formula:

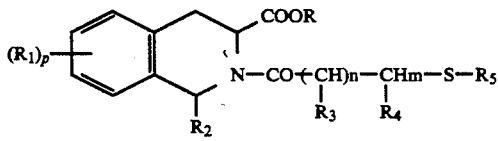

wherein
R=H, alkyl or alkali metal selected from the group consisting of sodium and potassium;
R₁=alkyl or alkoxy;
R₂=H, alkyl;
R₃=alkyl;
R₄=H;
R₅=H, alkanoyl, aroyl;
n=1;
m=1;
p=1, 2, 3;
or a pharmaceutically acceptable salt thereof.

28. A compound selected from the group consisting of N-(3 mercapto-2 methyl propanoyl)1,2,3,4 tetrahydro isoquinoline 3 carboxylic acid and N (3 mercapto propanoyl) 1,2,3,4 tetrahydro isoquinioline 3 carboxylic acid.

29. tert-Butyl N-(3'-acetylthio-2'-methylpropanoyl)-L-(1,2,3,4-tetrahydroisoquinoline-3-carboxylate.

30. N-(3'-Acetylthio-2'-methylpropanoyl)-L-(1,2,3,4-tetrahydroisoquinoline)-3-carboxylic acid.

31. N-(3'-Mercapto-2'-methylpropanoyl)-L-(1,2,3,4-tetrahydroisoquinoline)-3-carboxylic acid.

32. N-(3'-Acetylthio-2'-methylpropanoyl)L-6,7-dihydroxy-1,2,3,4-tetrahydroisoquinoline-3-carboxylic acid.

33. N-(3'-Acetylthio-2'-methylpropanoyl)-L-6,7-dimethoxy-1,2,3,4-tetrahydroisoquinoline-3-carboxylic acid.

34. N-(3'-Acetylthio-2'-methylpropanoyl)-L-7-chloro-1,2,3,4-tetrahydroisoquinoline-3-carboxylic acid.

35. N-(3'-Mercapto-2'-methylpropanoyl)-L-6,7-dimethoxy-1,2,3,4-tetrahydroisoquinoline-3-carboxylic acid.

36. N-(3'-Mercapto-2'-methylpropanoyl)-L-7-hydroxy-6-methoxy-1,2,3,4-tetrahydroisoquinoline-3-carboxylic acid.

37. N-(3'-Acetylthio-2'-methylpropanoyl)-6,7-dimethoxy-1,2,3,4-tetrahydroisoquinoline-1-carboxylic acid 38. N-(3'-Mercapto-2'-methylpropanoyl)-L-3-methyl-1,2,3,4-tetrahydroisoquinoline-3-carboxylic acid.

39. N-(3'-Acetylthio-2'-methylpropanoyl)-L-1-methyl-1,2,3,4-tetrahydroisoquinoline-3-carboxylic acid.

40. N-(3'-Mercapto-2'-methylpropanoyl)-L-1-methyl-1,2,3,4-tetrahydroisoquinoline-3-carboxylic acid.

41. N-(3'-Acetylthio-2'-methylpropanoyl)-1-(3'4'-dimethoxyphenyl)-1,2,3,4-tetrahydroisoquinoline-3-carboxylic acid.

42. N-(3'-Acetylthio-2'-methylpropanoyl)1,2-dihydroisoquinoline-1-carboxylic acid.

* * * * *

UNITED STATES PATENT AND TRADEMARK OFFICE
CERTIFICATE OF CORRECTION

PATENT NO. : 5,200,416
DATED : April 6, 1993
INVENTOR(S) : John T. Suh, et al.

It is certified that error appears in the above-identified patent and that said Letters Patent is hereby corrected as shown below:

Title page, item [57]:
    In the Abstract, line 20: "rad" should read --and--

Column 1, line 40: "OR ," should read --$OR_1$,--
    Column 1, line 40: "($CR_1R$" should read --$CR_1R_2$--
    Column 2, line 31; before "Ar" delete "." and insert --,--
    Column 2, line 36: "ar" should read --an--
    Column 7, line 64: "tert" should read --tert- --
    Column 8, line 46: "cluant" should read --eluant--
    Column 9, line 6: "8" should read -- --
    Column 9, line 29: "3'" should read --3'- --
    Column 9, line 30: "0.045" should read --0.0045--
    Column 10, line 11: "2'" should read --2'- --
    Column 10, line 16: "3'" should read --3'- --
    Column 10, lines 19 & 21: "8" should read -- --
    Column 10, line 25: 'N-(2'" should read --N-(3'--
    Column 10, line 25: "L-L" should read --L-1--
    Column 10, line 25: "methyl-3,4" should read --methyl-1,2,3,4--

UNITED STATES PATENT AND TRADEMARK OFFICE
CERTIFICATE OF CORRECTION

PATENT NO. : 5,200,416
DATED : April 6, 1993
INVENTOR(S) : John T. Suh, et al

Page 2 of 3

It is certified that error appears in the above-indentified patent and that said Letters Patent is hereby corrected as shown below:

Column 10, line 32: "2'6;" should read --2'6'--

Column 12, line 12, Claim 18: "$X_3$" should read --$X_1$--

Column 13, line 33, Claim 26: "alkylamino" should read --dialkylamino--

Column 13, line 37, Claim 27: "CHm" should read --(CHm)--

UNITED STATES PATENT AND TRADEMARK OFFICE
CERTIFICATE OF CORRECTION

PATENT NO. : 5,200,416
DATED : April 6, 1993
INVENTOR(S) : John T. Suh, et al

It is certified that error appears in the above-indentified patent and that said Letters Patent is hereby corrected as shown below:

Column 14, lines 9-11, Claim 28: "N-(3 mercapto-2 methyl propanoyl(1,2,3,4 tetrahydro isoquinoline 3 carboxylic acid and N (3 mercapto propanoyl) 1,2,3,4 tetrahydro isoquinoline 3 carboxylic" should read --N-3-mercapto-2- -methyl propanoyl(1,2,3,4-tetrahydro-isoquinoline-3-carboxylic acid and N-(3-mercapto propanoyl) 1,2,3,4-tetrahydro isoquinoline-3-carboxylic--

Column 14, line 19, Claim 32: before "L" insert -- - --

Column 14, line 33, Claim 37: after "acid" insert --.--

Signed and Sealed this

First Day of March, 1994

Attest:

BRUCE LEHMAN

Attesting Officer     Commissioner of Patents and Trademarks